United States Patent
Kim et al.

(10) Patent No.: US 12,239,395 B2
(45) Date of Patent: Mar. 4, 2025

(54) METHOD FOR ACQUIRING SURGERY DATA IN UNITS OF SUB-BLOCKS AND DEVICE THEREFOR

(71) Applicant: MEERE COMPANY INC., Hwaseong-si (KR)

(72) Inventors: Hyung Joo Kim, Seongnam-si (KR); You Jin Lee, Suwon-si (KR); Yo An Lim, Hwaseong-si (KR)

(73) Assignee: Meere Company Inc., Hwaseong-si (KR)

( * ) Notice: Subject to any disclaimer, the term of this patent is extended or adjusted under 35 U.S.C. 154(b) by 450 days.

(21) Appl. No.: 17/753,542

(22) PCT Filed: Aug. 3, 2020

(86) PCT No.: PCT/KR2020/010213
§ 371 (c)(1),
(2) Date: Mar. 7, 2022

(87) PCT Pub. No.: WO2021/049761
PCT Pub. Date: Mar. 18, 2021

(65) Prior Publication Data
US 2022/0331024 A1    Oct. 20, 2022

(30) Foreign Application Priority Data

Sep. 9, 2019   (KR) .......................... 10-2019-0111564

(51) Int. Cl.
*A61B 34/30*    (2016.01)
*G05B 19/4155*    (2006.01)

(52) U.S. Cl.
CPC .......... *A61B 34/30* (2016.02); *G05B 19/4155* (2013.01); *G05B 2219/40415* (2013.01)

(58) Field of Classification Search
CPC ............ A61B 34/30; A61B 2034/2068; A61B 2034/2074; A61B 34/20; A61B 34/00;
(Continued)

(56) References Cited

U.S. PATENT DOCUMENTS 9,211,643 B1 *  12/2015  Shirakyan ............. B25J 9/1674
9,434,069 B1 *   9/2016  Edsinger ............... B25J 9/1664
(Continued)

FOREIGN PATENT DOCUMENTS

KR    10-2012-0095586 A    8/2012
KR    10-2013-0104097 A    9/2013
(Continued)

OTHER PUBLICATIONS

International Search Report and Written Opinion mailed Apr. 5, 2021 in International Application No. PCT/KR2020/010213. (*English translation of ISR.*).

*Primary Examiner* — Abby Y Lin
*Assistant Examiner* — Esvinder Singh
(74) *Attorney, Agent, or Firm* — Knobbe, Martens, Olson, & Bear, LLP

(57) ABSTRACT

This application relates to a surgical data acquisition method. In one aspect, the surgical data acquisition method includes acquiring information about movement of a surgical robot, and dividing a hexahedral block including a maximum movement range of the surgical robot into a plurality of sub-blocks of a specified number. The method may also include storing, for each of the plurality of sub-blocks, information on a sub-block corresponding to a position in which the surgical robot has moved and information about the movement of the surgical robot within the sub-block.

17 Claims, 10 Drawing Sheets

(58) Field of Classification Search
CPC .............. A61B 2034/107; A61B 34/10; A61B 2034/2046; A61B 34/70; A61B 34/72; A61B 2090/365; A61B 2090/366; G05B 19/4155; G05B 2219/40415; G05B 2219/45117; G05B 2219/39449; G05B 2219/39451; G05B 2219/49137; G05B 2219/49157; G05B 2219/42272; B25J 9/1674; B25J 9/1628; B25J 9/163; B25J 9/1656; B25J 9/1664; B25J 9/1666; B25J 9/1676; G16H 20/40

See application file for complete search history.

(56) References Cited

U.S. PATENT DOCUMENTS

| | | | |
|---|---|---|---|
| 11,986,246 B2* | 5/2024 | Roldan | G16H 20/40 |
| 2017/0129100 A1 | 5/2017 | Takeda | |
| 2017/0277167 A1* | 9/2017 | Noda | B25J 9/1643 |
| 2017/0333137 A1 | 11/2017 | Roessler | |
| 2020/0375662 A1 | 12/2020 | Lee et al. | |

FOREIGN PATENT DOCUMENTS

| | | |
|---|---|---|
| KR | 10-2019-0010860 A | 1/2019 |
| KR | 10-2019-0080702 A | 7/2019 |

* cited by examiner

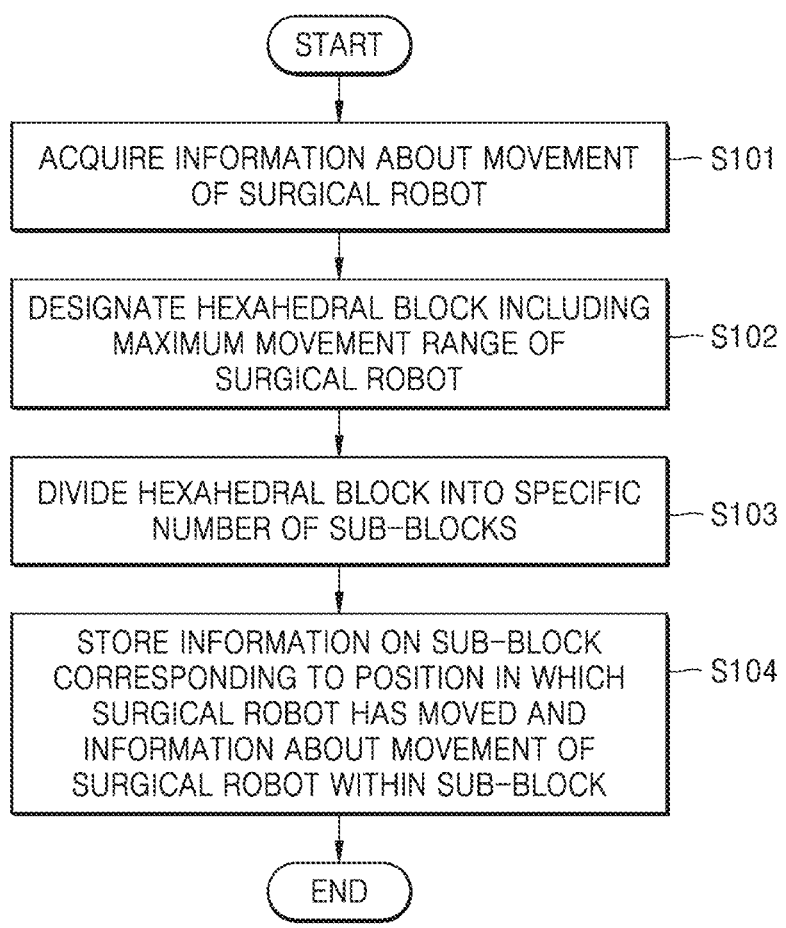

FIG. 8

| SUB-BLOCK | MOVEMENT SPEED | MOVEMENT DISTANCE | MOVEMENT TIME |
|---|---|---|---|
| $B_1$ | $V_1$ | $D_1$ | $T_1$ |
| $B_2$ | $V_2$ | $D_2$ | $T_2$ |
| $B_3$ | $V_3$ | $D_3$ | $T_3$ |
| $B_4$ | $V_4$ | $D_4$ | $T_4$ |
| $B_5$ | $V_5$ | $D_5$ | $T_5$ |
| ⋮ | ⋮ | ⋮ | ⋮ |

METHOD FOR ACQUIRING SURGERY DATA IN UNITS OF SUB-BLOCKS AND DEVICE THEREFOR

The present application is a U.S. national phase application under 35 U.S.C. § 371 of International Application No. PCT/KR2020/010213, filed on Aug. 3, 2020, which claims the benefit of Korean Patent Application No. 10-2019-0111564 filed on Sep. 9, 2019 in the Korean Intellectual Property Office, the entire disclosure of each of which is incorporated herein by reference.

TECHNICAL FIELD

The present disclosure relates to a surgical data acquisition method. More specifically, it relates to a method of acquiring surgical data using a relative coordinate of a surgical site.

BACKGROUND ART

A log data of a surgical robot generated as a surgery is performed using the surgical robot includes absolute coordinate information about a position where the surgical robot moved. Therefore, despite a surgery on a same site, the shape and size of the surgical site are different for each individual, so surgical data acquired through surgery on a specific person may not be used equally for other people. Therefore, it is required to provide a technology securing surgical data in a form applicable to various surgical environments.

DESCRIPTION OF EMBODIMENTS

Technical Problem

An object of the present disclosure is to provide a method and device for acquiring surgical data that are easy to analyze and utilize for log data generated by a surgical robot.

The technical problems of the present disclosure are not limited to the technical problems mentioned above, and other technical problems not mentioned will be clearly understood by those skilled in the art of the present disclosure from the description below.

Technical Solution to Problem

For solving the above technical problem, a surgical data acquisition method according to an embodiment of the present disclosure may include acquiring information about movement of a surgical robot, designating a hexahedral block including a maximum movement range of the surgical robot, dividing the hexahedral block into a plurality of sub-blocks of a specified number, and storing, for each of the plurality of sub-blocks, information on a sub-block corresponding to a position in which the surgical robot has moved and information about the movement of the surgical robot within the sub-block.

The dividing the hexahedral block according to an embodiment into the plurality of sub-blocks of the specified number may determine the specified number based on a surgical site corresponding to the hexahedral block.

All of the divided sub-blocks of the surgical data acquisition method according to one embodiment may have a same size.

The information about the movement of the surgical robot according to an embodiment may include information about at least one of movement coordinate, movement distance, movement time and movement velocity of the surgical robot.

The information about the movement of the surgical robot according to an embodiment may be information about movement of a distal end of a driving portion of the surgical robot.

The movement coordinate of the surgical robot according to an embodiment may be a relative coordinate acquired based on a position of the sub-block in the hexahedral block and a position of the distal end of the driving portion of the surgical robot in the sub-block.

The storing according to an embodiment may include storing a data pair including an identification value of the sub-block designated based on a position of the sub-block as a key and the information about the movement of the surgical robot within the sub-block as a value for each of the plurality of sub-blocks.

The acquiring according to an embodiment may include acquiring the information about the movement of the surgical robot at a time unit designated based on a surgical site.

For solving the above technical problem, a surgical data acquisition device according to another embodiment of the present disclosure may an acquisition unit acquiring information about movement of a surgical robot, a designation unit designating a hexahedral block including a maximum movement range of the surgical robot, a division unit dividing the hexahedral block into a plurality of sub-blocks of a specified number, and a storage unit storing information on a sub-block corresponding to a position in which the surgical robot has moved and information about the movement of the surgical robot within the sub-block for each of the plurality of sub-blocks.

BRIEF DESCRIPTION OF DRAWINGS

FIG. 1 is a flowchart of a surgical data acquisition method according to an embodiment of the present disclosure.

FIG. 8 is an exemplary view for explaining information about the movement of the surgical robot according to an embodiment of the present disclosure.

MODE FOR INVENTION

Figure 2A:
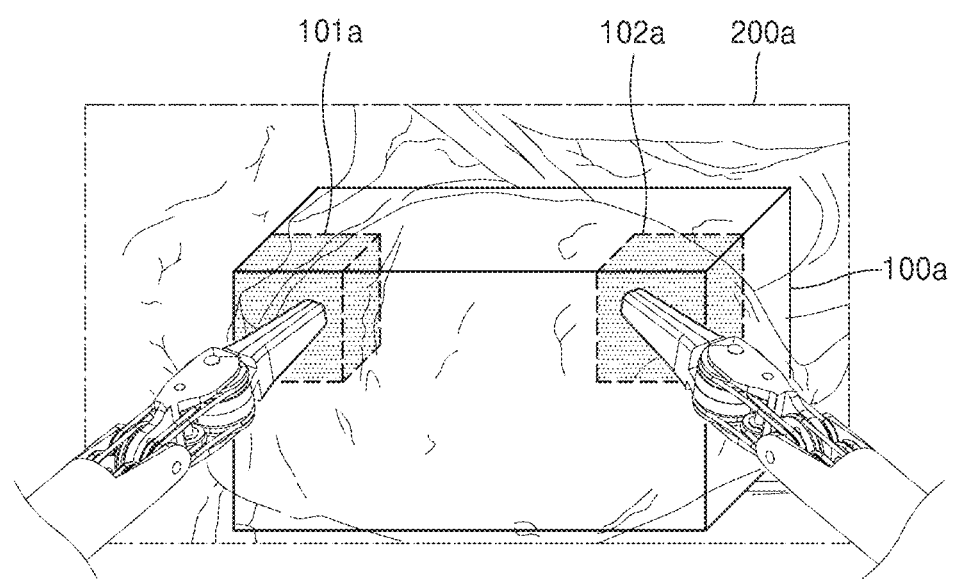
FIGS. 2A and 2B are conceptual views for explaining the surgical data acquisition method according to an embodiment of the present disclosure.

The detailed description of the present disclosure set forth below refers to the accompanying drawings, which show by way of illustration specific embodiments in which the present disclosure may be practiced. These embodiments are described in sufficient detail to enable any person skilled in the art to practice the present disclosure. It should be understood that various embodiments of the present disclosure are different but need not be mutually exclusive. For example, certain shapes, structures, and characteristics described herein may be implemented with changes from one embodiment to another without departing from the spirit and scope of the present disclosure. In addition, it should be understood that the location or arrangement of individual components within each embodiment may be changed without departing from the spirit and scope of the present disclosure. Accordingly, the following detailed description is not to be taken in a limiting sense, and the scope of the present disclosure should be taken to cover the scope of the claims and all equivalents thereto. In the drawings, like reference numerals refer to the same or similar elements throughout the various aspects.

Hereinafter, various embodiments of the present disclosure will be described in detail with reference to the accompanying drawings so that those of ordinary skill in the art to which the present disclosure pertains can easily practice the present disclosure.

When surgery is performed using a surgical robot, a large amount of log data is generated as the surgical robot is operated. A surgical data acquisition method according to some embodiments of the present disclosure may acquire relative coordinate-based surgical data that may be used for various individuals by using a vast amount of log data generated from a surgical robot.

Hereinafter, a surgical data acquisition method according to an embodiment of the present disclosure will be described with reference to FIG. 1.

In operation S101, information about movement of a surgical robot may be acquired. The information about the movement of the surgical robot is information generated according to the movement of the surgical robot within a surgical site, and may include information about the movement of the surgical robot. For example, the information about the movement of the surgical robot may be acquired in a form of log data generated by a computing device of the surgical robot. The log data may include data collection time information, information about pitch, roll, and yaw of the surgical robot, and information about coordinate of the surgical robot. However, note that the log data is only an example of the information about movement of the surgical robot, and various types of movement information may be acquired depending on a type of robot, a work performed by the robot, and a purpose of the robot. A detailed description will be given later with reference to FIG. 4.

In addition, since most surgeries are performed using a distal end of the surgical robot, the information about the movement of the surgical robot according to an embodiment may be movement information acquired based on a distal end of a driving portion of the surgical robot. However, the information about the movement of the surgical robot according to some embodiments of the present disclosure is not limited thereto, and may be movement information acquired based on a portion designated by a user of the driving portion of the surgical robot.

In operation S102, a hexahedral block including a maximum movement range of the surgical robot may be designated. Specifically, a size and shape of the hexahedral block may be determined, and a boundary value of the hexahedral block may be determined according to an embodiment. An inner area of the hexahedral block may include the maximum movement range of the surgical robot within the surgical site. Therefore, according to one embodiment, the boundary value of the hexahedral block may be designated to include all movement trajectories of the surgical robot using the log data of the surgical robot. A detailed description of how the boundary value of the hexahedral block is designated will be described later with reference to FIG. 3.

Hereinafter, in order to clarify the explanation of the coordinate of the surgical robot, the shape of the block including the maximum movement range of the surgical robot is described using the hexahedral block, but note that the hexahedral is only an example of the shape of the block including the maximum movement range of the surgical robot, and the shape of the block including the maximum movement range of the surgical robot according to some embodiments of the present disclosure may be various shapes that may be easily changed by a person skilled in the art.

In operation S103, the hexahedral block including the maximum movement range of the surgical robot may be divided into a plurality of sub-blocks of a specified number. The number of divided plurality of sub-blocks may be specified based on the surgical site. That is, the hexahedral blocks for the same surgical site are divided into equal numbers.

For example, when acquiring data of a surgical robot used for human liver surgery, the hexahedral block is designated to include the range in which the surgical robot moves in the liver, and may be divided into 1000 sub-blocks. At this time, even when data of a surgical robot used for other people's liver surgery is acquired, the hexahedral block may be divided into 1000 sub-blocks.

Therefore, even if the surgical data acquired from various individuals are surgical data for the same surgical site, the number of sub-blocks is the same regardless of the size of the hexahedral block, and the plurality of sub-blocks may correspond one-to-one with the sub-blocks of another individual, respectively. The individual refers to each of surgical subjects, for example, the individual may be a human or an animal. The individual includes at least one surgical site, and surgical data of a surgical site acquired from a specific individual may be used for surgery on the same surgical site of another individual.

In operation S104, information on the sub-block corresponding to a position in which the surgical robot has moved and information about the movement of the surgical robot within the sub-block may be stored. In an embodiment, the stored information may be in a form of a data pair including identification value of the sub-block as a key and the information about the movement of the surgical robot within the sub-block as a value. For each sub-blocks, the information about the movement of the surgical robot corresponding to the sub-block is stored together, making it easier to acquire and analyze the surgical data for a specific sub-block. That is movement data of the surgical robot acquired for each sub-block is highly reusable, so it may be used as data for various analysis techniques on the surgical site, and may also be used as training data for machine learning.

Hereinafter, a method in which the surgical data acquisition method according to an embodiment is applied to different individuals will be described in detail with reference to FIGS. 2A and 2B.

When log data of a surgical robot for the same surgical site is obtained for different individuals, a size and shape of a first individual's surgical site 200a may be different from those of a second individual's surgical site 200b as illustrated. Even with surgical data for the same surgical site, there is a limit that the absolute coordinate of the movement of the surgical robot acquired from the first individual may not be equally applied to the surgical site of the second individual.

Therefore, a surgical data acquisition method according to some embodiments of the present disclosure designates a hexahedral block 100a or 100b including a maximum movement range of the surgical robot within the surgical site, and may divide the hexahedral block 100a or 100b to sub-blocks 101a, 101b, 102a, and 102b of a specified number.

Figure 2B:
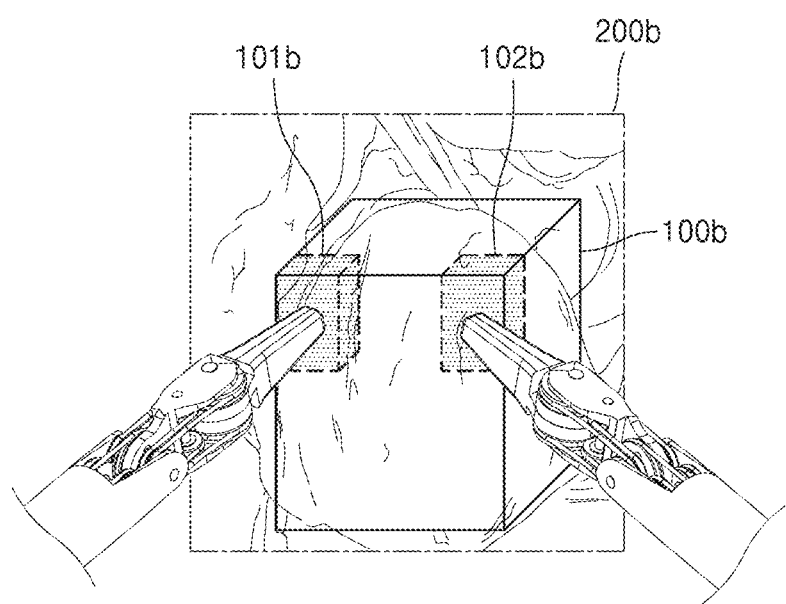

Referring to the drawings, the sizes of the hexahedral blocks 100a and 100b illustrated in FIGS. 2A and 2B are different from each other, but they are divided into the same number of sub-blocks.

In addition, a plurality of sub-blocks 101a and 102a included in a hexahedral block 100a corresponding to the surgical site 200a of the first individual may corresponding to a plurality of sub-blocks 101b and 102b included in a hexahedral block 100b corresponding to the same surgical site 200b of the second individual, respectively. Therefore, information about the movement of the surgical robot within an upper left sub-block 101a of the first individual may correspond to information about the movement of the surgical robot within an upper left sub-block 101b for the same surgical site of the second individual, and information about the movement of the surgical robot within an upper right sub-block 102a of the first individual may correspond to information about the movement of the surgical robot within an upper right sub-block 102b for the same surgical site of the second individual.

Figure 3:
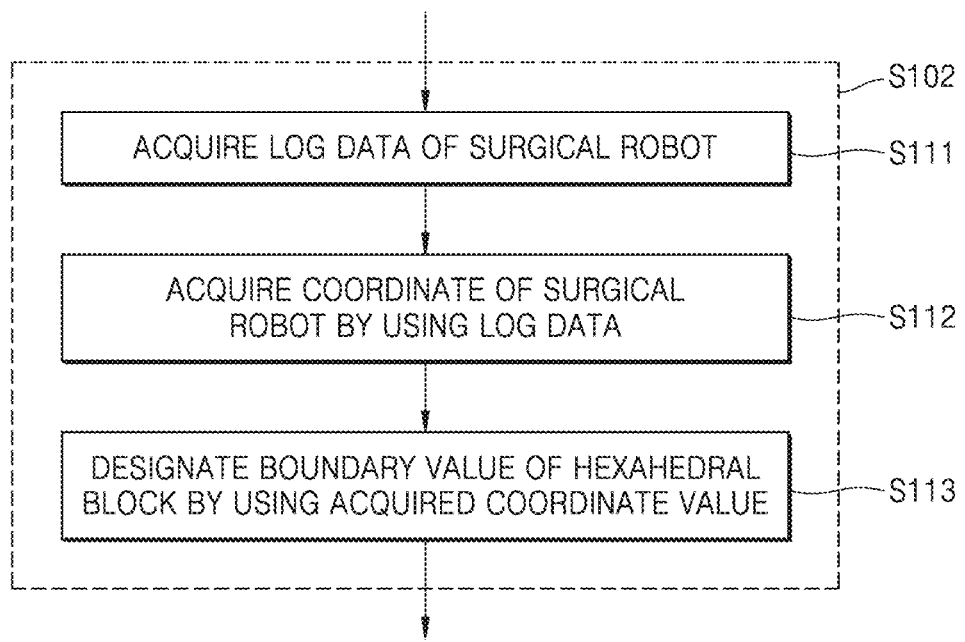
FIG. 3 is a flowchart for describing in detail some operations of FIG. 1.

Hereinafter, a method of designating the hexahedral block according to some embodiments of the present disclosure will be described in detail with reference to FIG. 3.

In operation S111, coordinates of the surgical robot may be acquired using the acquired log data. For example, x, y, and z coordinates may be calculated using forward kinematics, which is robot kinematics, with joint values acquired from the log data. Using the joint values, the coordinates (position) and orientation of the surgical robot may be acquired.

In operation S112, a boundary value of the hexahedral block may be designated using the coordinate values of the surgical robot. In one embodiment, the boundary value of the hexahedral block may be determined by using $x_{max}$, which is a maximum value of x, and $x_{min}$, which is a minimum value of x, $y_{max}$, which is a maximum value of y, and $y_{min}$, which is a minimum value of y, and $z_{max}$, which is a maximum value of z, and $z_{min}$, which is a minimum value of z, among the coordinates according to the movement trajectory of the surgical robot.

However, it should be noted that the above log data is only an example of information about movement of the surgical robot, and various types of movement information may be acquired depending on a type of robot, a work performed by the robot, and a purpose of the robot.

Hereinafter, information about the movement of the surgical robot according to an embodiment of the present disclosure will be described in detail with reference to FIG. 4.

Figure 4:
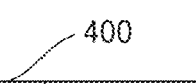
FIG. 4 is an exemplary diagram for explaining log data of a surgical robot according to an embodiment of the present disclosure.

A log data 400 of FIG. 4 is an example of the log data of the surgical robot. As illustrated, the log data 400 acquired from the surgical robot may include time information and information about movement of the surgical robot.

The surgical data acquisition method according to an embodiment may acquire the log data of the surgical robot in a time unit designated based on the surgical site. For example, a log data acquisition cycle when the surgical site is small may be shorter than a log data acquisition cycle when the surgical site is large. When the log data acquisition cycle is changed according to the surgical site, the present embodiment may efficiently use computing resources.

In addition, the coordinates of the x, y, and z values of the surgical robot may be acquired every cycle by using the joint values of log data. In one embodiment, the coordinate of the surgical robot may be a coordinate for the position of the distal end of the driving portion of the surgical robot, or may be a coordinate for a designated part of the surgical robot.

Hereinafter, a method of storing information about the movement of the surgical robot for each sub-block will be described in detail with reference to FIGS. 5 and 6.

As described above, by defining the hexahedral block and designating the movement coordinate of the surgical robot as the relative coordinate, the information about the movement of the surgical robot may be easily utilized regardless of the size of the hexahedral block. Hereinafter, a method of storing and utilizing the acquired information about the movement of the surgical robot will be described in detail.

Figure 5:
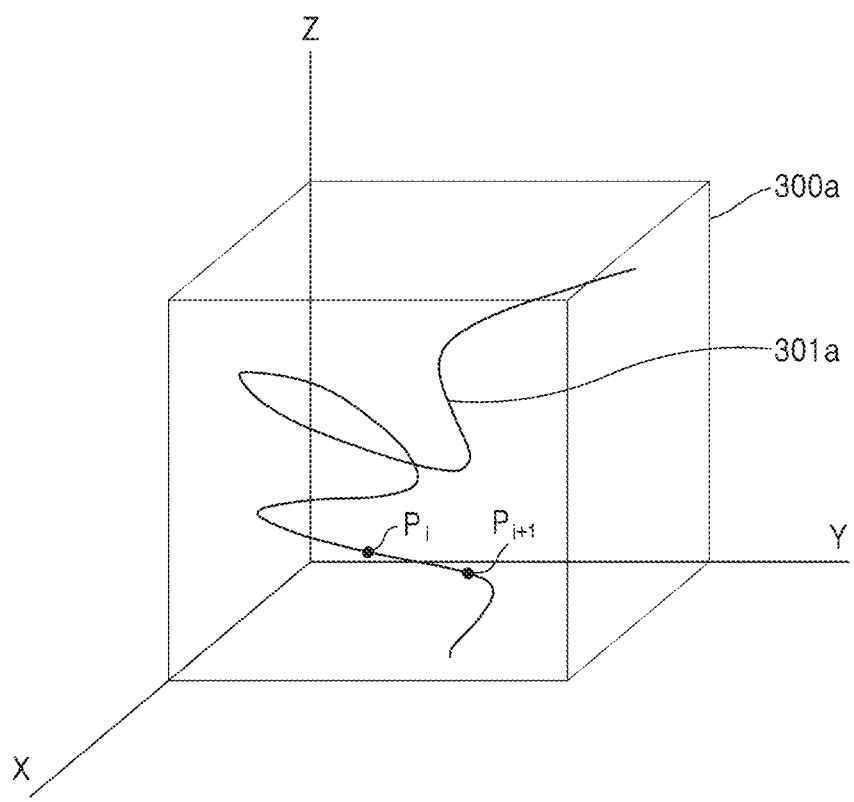
FIG. 5 is a conceptual diagram for explaining a hexahedral block according to an embodiment of the present disclosure.

Referring to FIG. 5, when information about the movement of the surgical robot included in movement trajectory 301a of the surgical robot in an area inside a hexahedral block 300a is stored as one data, even when it is intended to acquire only information about the movement of the surgical robot corresponding to some area or a specific time period, there is a problem that the entire information about the movement of the surgical robot must be transmitted. In addition, even when the information about the movement of the surgical robot is used as a training data of a machine learning algorithm, there is a problem that all the information about the movement of the surgical robot for the entire surgical site must be input as the training data. When a size of data that may be transmitted at one time is large, a time complexity and space complexity of a computing operation using the data are inevitably very large.

Figure 6:
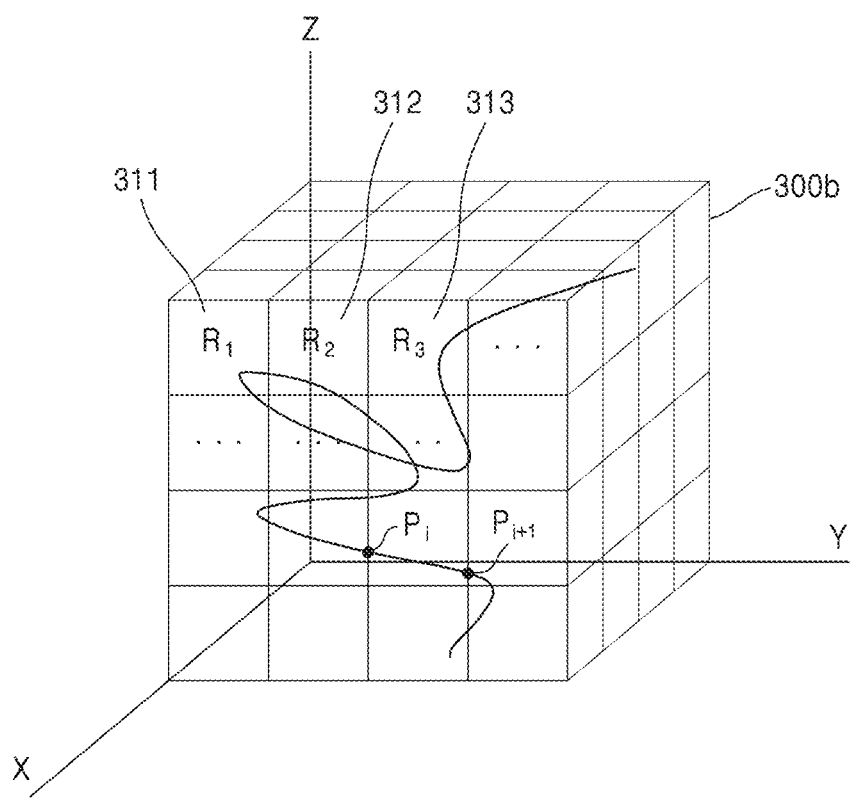
FIG. 6 is a conceptual diagram explaining a sub-block according to an embodiment of the present disclosure.

Accordingly, as illustrated in FIG. 6, the surgical data acquisition method according to some embodiments of the present disclosure divides a hexahedral block 300b corresponding to the surgical site into a plurality of sub-blocks 311, 312, 313. Surgical data according to an embodiment may be stored in a form in which, for each of the sub-blocks 311, 312, 313, identification value data of the sub-block designated based on a position of the sub-block and movement information data of the surgical robot within the sub-block are mapped. Therefore, when it is desired to acquire only information about the movement of the surgical robot for a specific part of the surgical site, only information about the movement of the surgical robot corresponding to a sub-block corresponding to the specific part may be acquired. In addition, the surgical data may be used as training data for machine learning that extracts features according to the position of the surgical site.

According to an embodiment, a division ratio of the plurality of sub-blocks may be specified according to the surgical site. For example, in the case of a specific surgical site, a size of the divided sub-blocks may all be the same. Since the division ratio of the sub-blocks is the same depending on the surgical site, surgical data for surgical sites of various sizes may be used as a basis of relative coordinates. At this time, when the acquired surgical data is used as training data for machine learning, information about the division ratio of the sub-block may also be used as the training data.

Figure 7:
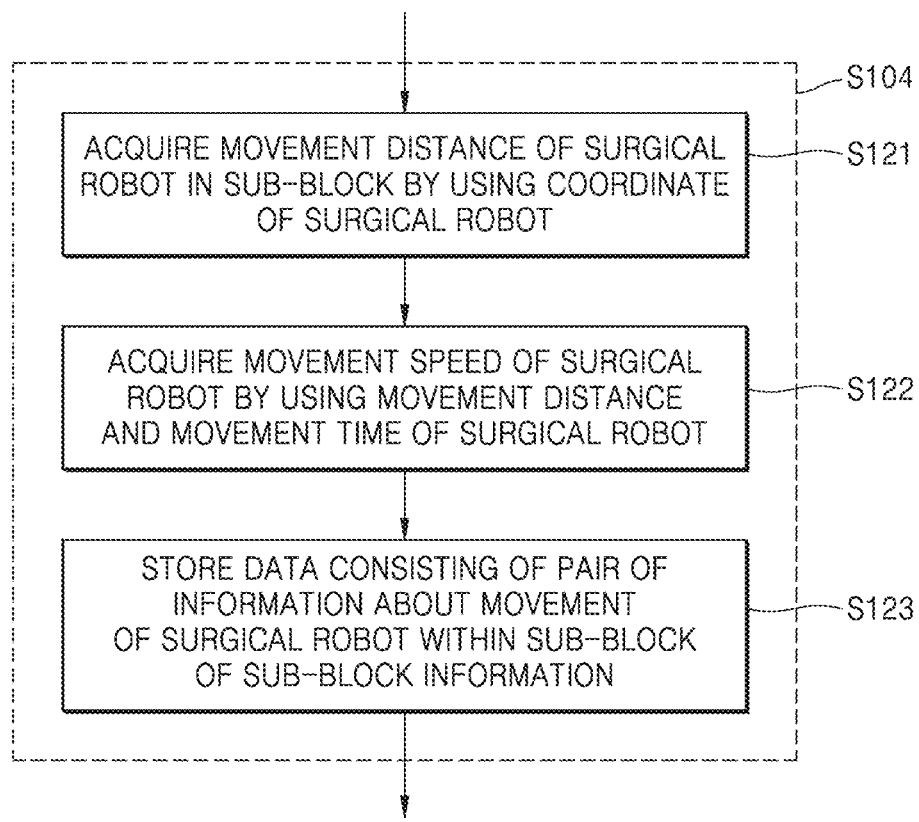
FIG. 7 is a flowchart for explaining in detail some operations of FIG. 1.

Hereinafter, the information about the movement of the surgical robot stored for each sub-block will be described in detail with reference to FIG. 7.

In operation S121, movement distance of the surgical robot in the sub-block may be acquired using the coordinate values of the surgical robot. For example, coordinates of Pi and Pi+1 present in the movement trajectory of the surgical robot illustrated in FIG. 6 are Pi(xi, yi, zi) and Pi+1(xi+1, yi+1, zi+1), respectively, the movement distance $D_i = \sqrt{(x_{i+1}-x_i)^2 + (y_{i+1}-y_i)^2 + (z_{i+1}-z_i)^2}$ of the surgical robot within the sub-block may be acquired by using each coordinate value.

In operation S122, movement speed of the surgical robot may be acquired using the movement distance of the surgical robot and movement time of the surgical robot. The movement time of the surgical robot according to an embodiment may be acquired by using the acquisition cycle of log data.

In addition, the movement speed of the surgical robot in each sub-block may be acquired by using the surgical robot's log data acquisition interval 'Ti+1−Ti' as the surgical robot's movement time. For example, the log data acquisition interval of the surgical robot may be 5 ms. In addition, the surgical robot's movement speed Vi in each sub-block may be acquired by dividing movement distance Di by movement time 'Ti+1−Ti'.

In operation S123, data consisting of a pair of the sub-block's information and the surgical robot's movement information in the sub-block may be stored. The information about the movement of the surgical robot may include information on the movement distance, the movement time, and the movement speed of the robot. Since the detailed description has been described above, it is omitted to avoid duplicate description.

FIG. 8 is an example of a data table in which the information about the movement of the surgical robot is stored for each of the plurality of sub-blocks according to an embodiment. Sub-block information B1, B2, B3, . . . , Bn may include information about identification value of the sub-block, and the identification value of the sub-block may be a unique value determined according to the position of the sub-block, in this case, the sub-block information may be the key of the data pair.

As described above, the information about the movement of the surgical robot may include the movement speed, movement distance, and movement time of the surgical robot. Not limited to this, the information about the movement of the surgical robot may further include information on movement coordinate and movement orientation of the surgical robot. In addition, the information about the movement of the surgical robot may be the value having the sub-block information as the key. However, it should be noted that the form of data including the information about the movement of the surgical robot according to some embodiments of the present disclosure may be in the form of various data structures such as a hash table and a map that may be transformed by a person skilled in the art.

Figure 9:
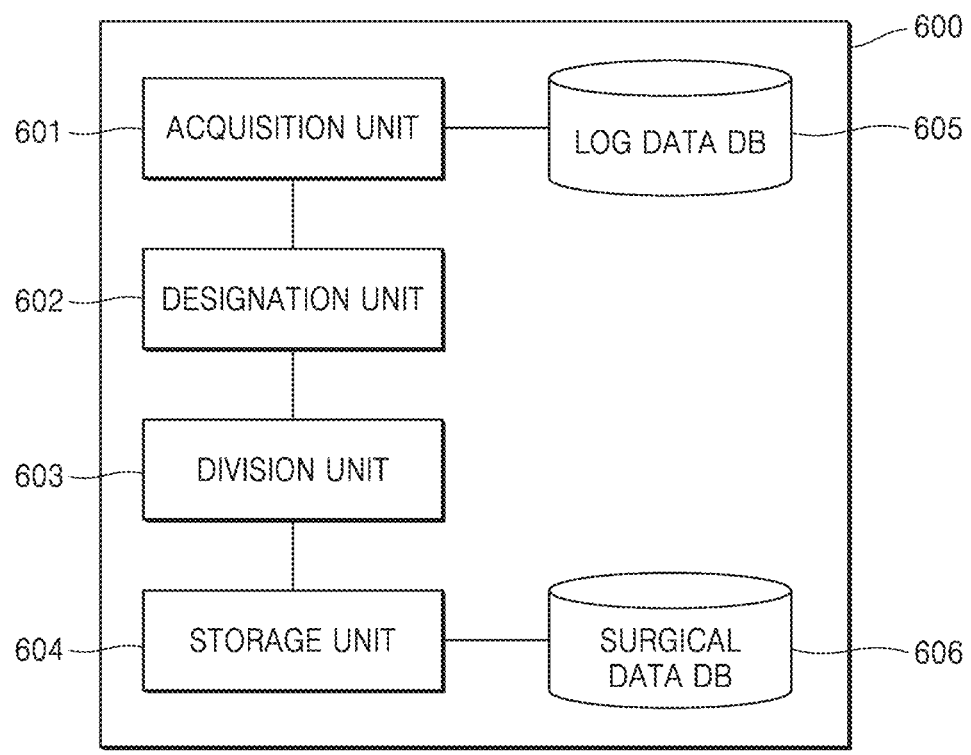
FIG. 9 is a block diagram for explaining configuration and operation of a surgical data acquisition device according to an embodiment of the present disclosure.

FIG. 9 is a block diagram for explaining configuration and operation of a surgical data acquisition device according to an embodiment of the present disclosure.

A surgical data acquisition device 600 according to an embodiment of the present disclosure may include an acquisition unit 601, a designation unit 602, a division unit 603, a storage unit 604, a log data DB 605, and a surgical data DB 606.

In one embodiment, the acquisition unit 601 may acquire the information about the movement of the surgical robot from the log data DB 605. The movement information may include information about at least one of the movement coordinate, movement distance, movement time, and movement velocity of the surgical robot, and may be information about the movement of the distal end of the driving portion of the surgical robot. Also, the movement coordinate may be the relative coordinate acquired based on the position of the sub-block in the hexahedral block and the position of the distal end of the driving portion of the surgical robot in the sub-block.

In one embodiment, the log data DB 605 may store the log data acquired by the surgical robot. The log data may be acquired and stored at the time unit designated based on the surgical site.

In one embodiment, the designation unit 602 may designate the hexahedral block including the maximum movement range of the surgical robot. The boundary value of the hexahedral block may be designated to include all movement trajectories of the surgical robot using the log data of the surgical robot.

In one embodiment, the division unit 603 may divide the hexahedral block into the plurality of sub-blocks of the specified number. In addition, the division unit may determine the specified number based on the surgical site, and the size of the divided sub-blocks may all be the same.

In one embodiment, for each of the plurality of sub-blocks, the storage unit 604 may store information on the sub-block corresponding to the position in which the surgical robot has moved and the information about the movement of the surgical robot within the sub-block into the surgical data DB 606.

In one embodiment, for each of the plurality of sub-blocks, the surgical data DB 606 may store the data pair including the identification value of the sub-block designated based on the position of the sub-block as the key and the information about the movement of the surgical robot within the sub-block as the value.

The specific implementations described in the present disclosure are examples, and do not limit the scope of the present disclosure in any way. For brevity of the specification, descriptions of conventional electronic components, control systems, software, and other functional aspects of the systems may be omitted. In addition, the connection or connection members of lines between the components shown in the drawings illustratively represent functional connections and/or physical or circuit connections, and in an actual device, various functional connections, physical connections that are replaceable or additional may be referred to as connections, or circuit connections. In addition, unless there is a specific reference such as "essential" or "importantly", it may not be a necessary component for the application of the present disclosure.

In the specification of the present disclosure (especially in the claims), the use of the term "above" and similar referential terms may correspond to both the singular and the plural. In addition, when a range is described in the present disclosure, it includes the disclosure to which individual values belonging to the range are applied, and if there is no description to the contrary, each individual value constituting the range is described in the detailed description of the disclosure. Finally, the steps constituting the method according to the present disclosure may be performed in an appropriate order unless the order is explicitly stated or there is no description to the contrary. The present disclosure is not necessarily limited to the order in which the steps are described. The use of all examples or exemplary terminology (e.g., etc.) in the present disclosure is merely for the purpose of describing the present disclosure in detail, and, unless limited by the claims, the scope of the present disclosure is due to the examples or exemplary terminology.

is not limited. In addition, those skilled in the art will recognize that various modifications, combinations, and changes can be made in accordance with design conditions and factors within the scope of the appended claims or their equivalents.

The embodiments according to the present disclosure described above may be implemented in the form of program instructions that can be executed through various computer components and recorded in a computer-readable recording medium. The computer-readable recording medium may include program instructions, data files, data structures, etc. alone or in combination. The program instructions recorded on the computer-readable recording medium may be specially designed and configured for the present disclosure, or may be known and available to those skilled in the art of computer software. Examples of computer-readable recording media include hard disks, magnetic media such as floppy disks and magnetic tapes, optical recording media such as CD-ROMs and DVDs, and magneto-optical media such as floppy disks. medium), and hardware devices specially configured to store and execute program instructions, such as ROM, RAM, flash memory, and the like. Examples of program instructions include not only machine language codes such as those generated by a compiler, but also high-level language codes that can be executed by a computer using an interpreter or the like. A hardware device may be converted into one or more software modules to perform processing according to the present disclosure, and vice versa.

In the above, the present disclosure has been described with specific details such as specific components and limited embodiments and drawings, but these are provided to help a more general understanding of the present disclosure, and the present disclosure is not limited to the above embodiments, and the present disclosure is not limited to the present disclosure. Those of ordinary skill in the art to which the disclosure pertains can devise various modifications and changes from these descriptions.

Accordingly, the spirit of the present disclosure should not be limited to the above-described embodiments, and, as well as the claims to be described later, all ranges equivalent to or changed from these claims fall within the scope of the spirit of the present disclosure.

The invention claimed is:

1. A method of controlling a surgical robot, the method comprising:
   first acquiring information about movement of the surgical robot operating at a first surgical site of a first individual;
   designating a first hexahedral block including a first maximum movement range of the surgical robot operating at the first surgical site of the first individual;
   dividing the first hexahedral block into a first specified number of a plurality of first sub-blocks;
   first storing, for each of the plurality of first sub-blocks, first information on a first sub-block corresponding to a position in which the surgical robot has moved at the first surgical site of the first individual and information about the movement of the surgical robot within the first sub-block;
   second acquiring information about movement of the surgical robot operating at a second surgical site of a second individual different from the first individual, the second surgical site being the same in body location as the first surgical site;
   designating a second hexahedral block including a second maximum movement range of the surgical robot operating at the second surgical site of the second individual, the second maximum movement range being different from the first maximum movement range;
   dividing the second hexahedral block into a second specified number of a plurality of second sub-blocks, the second specified number being the same as the first specified number;
   second storing, for each of the plurality of second sub-blocks, second information on a second sub-block corresponding to a position in which the surgical robot has moved at the second surgical site of the second individual and information about the movement of the surgical robot within the second sub-block;
   training a machine learning algorithm for controlling the surgical robot with the first information and the second information; and
   controlling a driving portion of the surgical robot based on the trained machine learning algorithm to perform a surgery on the same surgical site of a third individual different from the first and second individuals.

2. The method of claim 1, wherein in the dividing, the specified number is determined based on a surgical site corresponding to the first or second hexahedral block.

3. The method of claim 2, wherein all of the first and second sub-blocks have the same size.

4. The method of claim 1, wherein the controlling comprises controlling the driving portion of the surgical robot with respect to at least one of a movement coordinate, a movement distance, a movement time, or a movement velocity of the surgical robot.

5. The method of claim 4, wherein the controlling comprises controlling movement of a distal end of the driving portion of the surgical robot.

6. The method of claim 5, wherein the movement coordinate of the surgical robot comprises a relative coordinate acquired based on a position of the sub-block in the first or second hexahedral block and a position of the distal end of the driving portion of the surgical robot in the sub-block.

7. The method of claim 1, wherein each of the first storing and the second storing comprises storing a data pair including an identification value of the sub-block designated based on a position of the sub-block as a key and the information about the movement of the surgical robot within the sub-block as a value for each of the plurality of sub-blocks.

8. The method of claim 1, wherein each of the first acquiring and the second acquiring comprises acquiring the information about the movement of the surgical robot at a time unit designated based on a surgical site.

9. A non-transitory computer-readable recording medium storing instructions, when executed by one or more processors, causing the one or more processors to perform the method of claim 1.

10. A surgical robot comprising:
    a memory storing instructions; and
    one or more processors configured to execute the instructions to:
    acquire information about movement of a surgical robot operating at a first surgical site of a first individual;
       designate a first hexahedral block including a first maximum movement range of the surgical robot operating at the first surgical site of the first individual;
       divide the first hexahedral block into a first specified number of a plurality of first sub-blocks;
       store, for each of the plurality of first sub-blocks, first information on a first sub-block corresponding to a position in which the surgical robot has moved at the first surgical site of the first individual and information about the movement of the surgical robot within the sub-block for each of the plurality of first sub-blocks;

acquire information about movement of the surgical robot operating at a second surgical site of a second individual different from the first individual, the second surgical site being the same in body location as the first surgical site;

designate a second hexahedral block including a second maximum movement range of the surgical robot operating at the second surgical site of the second individual, the second maximum movement range being different from the first maximum movement range;

divide the second hexahedral block into a second specified number of a plurality of second sub-blocks, the second specified number being the same as the first specified number;

store, for each of the plurality of second sub-blocks, second information on a sub-block corresponding to a position in which the surgical robot has moved at the second surgical site of the second individual and information about the movement of the surgical robot within the second sub-block;

train a machine learning algorithm for controlling the surgical robot with the first information and the second information; and control a driving portion of the surgical robot based on the trained machine learning algorithm to perform a surgery on the same surgical site of a third individual different from the first and second individuals.

11. The surgical robot of claim 10, wherein the one or more processors are configured to determine the specified number based on a surgical site corresponding to the first or second hexahedral block.

12. The surgical robot of claim 11, wherein all of the divided sub-blocks have the same size.

13. The surgical robot of claim 10, wherein the one or more processors are configured to control the driving portion of the surgical robot with respect to at least one of a movement coordinate, a movement distance, a movement time, or a movement velocity of the surgical robot.

14. The surgical robot of claim 13, wherein the one or more processors are configured to control movement of a distal end of the driving portion of the surgical robot.

15. The surgical robot of claim 13, wherein the movement coordinate of the surgical robot comprises a relative coordinate acquired based on a position of the sub-block in the first or second hexahedral block and a position of the distal end of the driving portion of the surgical robot in the sub-block.

16. The surgical robot of claim 10, wherein the one or more processors are configured to store a data pair including an identification value of the sub-block designated based on a position of the sub-block as a key and the information about the movement of the surgical robot within the sub-block as a value for each of the plurality of sub-blocks.

17. The surgical robot of claim 10, wherein the one or more processors are configured to acquire the information about the movement of the surgical robot in a time unit designated based on a surgical site.

* * * * *